United States Patent [19]
Balbierz et al.

[11] Patent Number: 6,059,771
[45] Date of Patent: *May 9, 2000

[54] STIFFENING MEMBER TO INCREASE FLUID FLOW WITHIN A MEDICAL DEVICE

[75] Inventors: Daniel J. Balbierz, Redwood City; Robert Bley, Menlo Park, both of Calif.

[73] Assignee: Johnson & Johnson Medical, Inc., Arlington, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/772,399

[22] Filed: Dec. 23, 1996

[51] Int. Cl.⁷ ..................................................... A61M 25/00
[52] U.S. Cl. ............................ 604/528; 604/524; 604/264
[58] Field of Search ..................................... 600/585, 435; 604/164, 280, 264, 265, 523, 528, 524

[56] References Cited

U.S. PATENT DOCUMENTS

| | | | |
|---|---|---|---|
| 4,253,462 | 3/1981 | Dutcher et al. | 128/303 R |
| 4,381,013 | 4/1983 | Dutcher | 128/785 |
| 4,498,482 | 2/1985 | Williams | 128/786 |
| 4,661,094 | 4/1987 | Simpson | 604/53 |
| 4,796,642 | 1/1989 | Harris | 128/772 |
| 4,850,960 | 7/1989 | Grayzel | 604/53 |
| 4,854,330 | 8/1989 | Evans, III et al. | 128/772 |
| 5,299,580 | 4/1994 | Atkinson et al. | 600/585 |
| 5,357,961 | 10/1994 | Fields et al. | 128/658 |
| 5,370,640 | 12/1994 | Kolff | 606/2 |
| 5,382,238 | 1/1995 | Abrahamson et al. | 604/170 |
| 5,413,560 | 5/1995 | Solar | 604/164 |
| 5,437,288 | 8/1995 | Schwartz et al. | 128/772 |
| 5,498,249 | 3/1996 | Quinn | 604/280 |
| 5,498,251 | 3/1996 | Dalton | 604/282 |

FOREIGN PATENT DOCUMENTS

| | | |
|---|---|---|
| 0563759 | 3/1993 | European Pat. Off. . |
| 0728496 | 8/1996 | European Pat. Off. . |
| WO9633654 | 10/1996 | WIPO . |

*Primary Examiner*—Wynn Wood Coggins
*Assistant Examiner*—Deborah Blyveis
*Attorney, Agent, or Firm*—Blakely, Sokoloff, Taylor & Zafman

[57] ABSTRACT

The present invention relates to a stiffening member, which is a stylet, that helps increase the fluid flow area within a catheter. In a preferred embodiment, the stylet is made of a single piece of flat rectangular stock that can be twisted to provide equal rigidity in all directions. A cross-section of the stylet reveals that the substantially flat rectangular shape of the stylet permits maximum fluid flow between the stylet and the catheter. This results in increased ease in manipulating and removing the stylet from the catheter. In addition, because the preferred embodiment of the stylet comprises a single element, it is easier to manufacture and should result in lower manufacturing costs. Moreover, the use of the present invention should also result in lower overall healthcare costs.

9 Claims, 8 Drawing Sheets

STIFFENING MEMBER TO INCREASE FLUID FLOW WITHIN A MEDICAL DEVICE

BACKGROUND OF THE INVENTION

1. Field of the Invention

The present invention relates generally to the field of medical devices. In particular, this invention pertains to a stylet that helps increase the rigidity of a medical device, particularly when the medical device is being inserted.

2. Description of related art

Numerous types of catheters are well-known in the prior art; for example, peripherally inserted central catheters (PICCs) are commonly used in the prior art. Peripherally inserted central catheters are used to access the vascular system. In particular, PICCs are used when long-term-vascular access is required (e.g., more than two weeks indwelling time in a patient) to avoid multiple injections of the patient. A PICC is a long catheter that is often inserted mid-way on a patient's arm and the end of the catheter is often placed in the superior vena cava of the heart. PICCs often provide access to a patient's vascular system for chemotherapy or other types of intravenous medication. Because the PICC must often travel through many natural obstacles in the venous/vascular system, the catheter must be soft and pliable for ease of navigation and to avoid trauma to a blood vessel. In addition, the catheter must also be made of bio-compatible materials so that it will not irritate a patient's veins during the catheter's long dwelling time.

Unfortunately, PICC lines made of a soft bio-compatible material are very difficult to insert into a patient because its soft or pliable construction causes the PICC to often collapse and bend before entering the patient's veins. In order to more quickly and efficiently insert a PICC, a flexible metal stylet (or guidewire) is used as a stiffening member inside the catheter during insertion. Once the catheter is placed inside the patient, the guidewire is removed. Guidewires, however, cause several problems. There is increased friction between the guidewire and the inner wall of the catheter since the catheter often makes many turns and twists before reaching its final destination. As a result, it is often difficult to manipulate and then remove the guidewire. Second, the use of the guidewire also introduces the possibility that the guidewire may perforate a catheter when it is forced against the catheter.

One solution to these problems is to flush the catheter before using it, during the insertion process to aid manipulation of the guidewire, and/or after the insertion process to assist removal of the guidewire. These flushing solutions often contain heparin and saline. The need for a flushing system and a stiffening member, such as a stylet, becomes even more significant as catheters decrease in diameter. A smaller catheter is often more beneficial for patients with small or fragile veins since a smaller catheter causes less trauma to the patient's veins. The use of smaller catheters has also necessitated that the guidewire or stylet be smaller. Yet stylets have not decreased in size to the degree needed. Consequently, the fluid flow area for the flushing solution is decreasing at the same time the need for the flushing solution and a larger fluid flow area are increasing. This is counterproductive.

Figure 1:
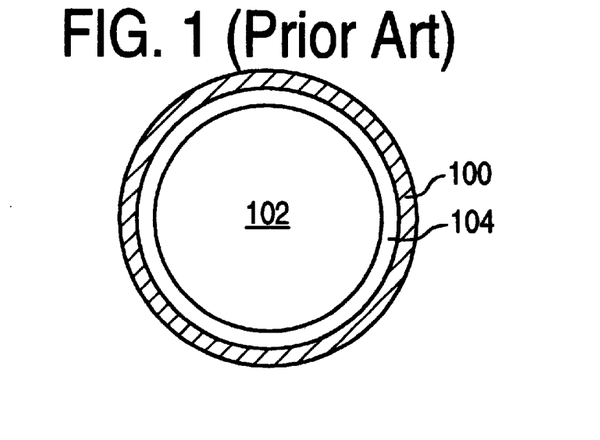
FIG. 1 illustrates a prior art guidewire (or stylet).
Figure 2A:
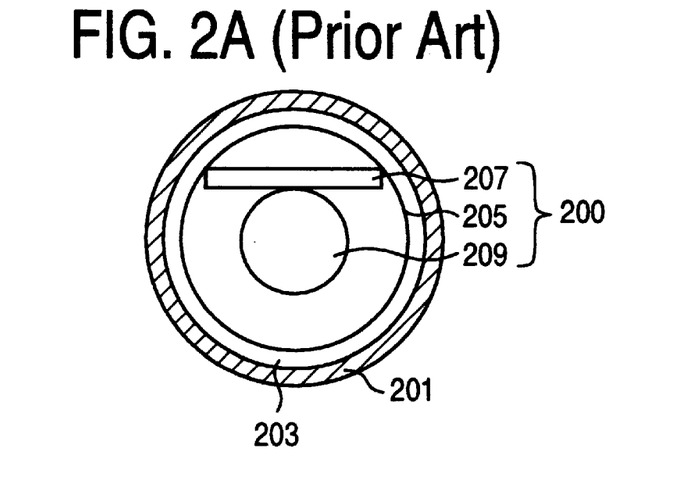
FIG. 2A illustrates a prior art guidewire made of three components.

Referring to FIG. 1, a cross-section of a prior art guidewire 102 is shown in a small catheter 100 with minimal space for the fluid flow area 104. In an exemplary catheter with a 0.035 inch diameter, a cross-sectional area of guidewire 102 occupies about 70% of the cross-sectional area of the lumen of catheter 100. Consequently, only about 30% of the cross-sectional area of catheter's 100 lumen is available as the fluid flow area 104. Another prior art embodiment of a guidewire 200 is shown in FIG. 2A. The guidewire 200 is made of three elements: a flat ribbon of material 207 adjacent to a core 209, both of which are disposed within a twisted-helical coil 205. The resulting fluid flow area 203 between the guidewire 200 and the catheter 201 is minimal.

Figure 2B:
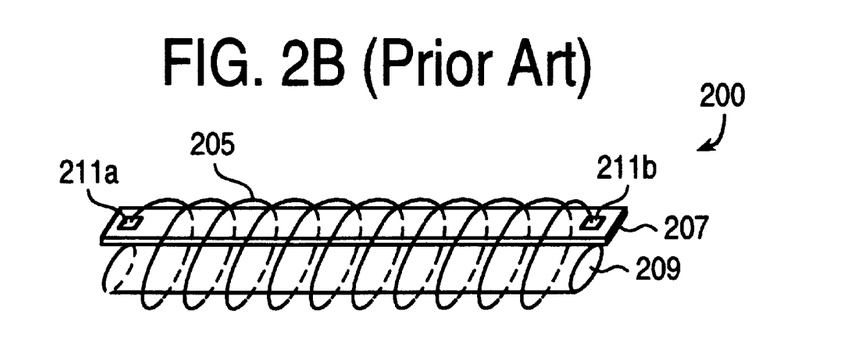
FIG. 2B is an exaggerated side view of FIG. 2A.

A side view of the guidewire 200 of FIG. 2A is illustrated in FIG. 2B. The helical coil 205 is welded on both ends of the ribbon 207 at 211a and 211b. The twists of the helical coil 205 are often not visible to the naked eye, but for the sake of clarity, the space between each of the coils in coil 205 have been exaggerated in FIG. 2B. The coil 205 often flexes as it twists and turns with the catheter 201. This allows some fluid to flow in between the coils 205 and around the core 209, which provides stiffness, and the flat ribbon 207. In addition, the core 209 can also be welded to the flat ribbon 207.

Figure 3:
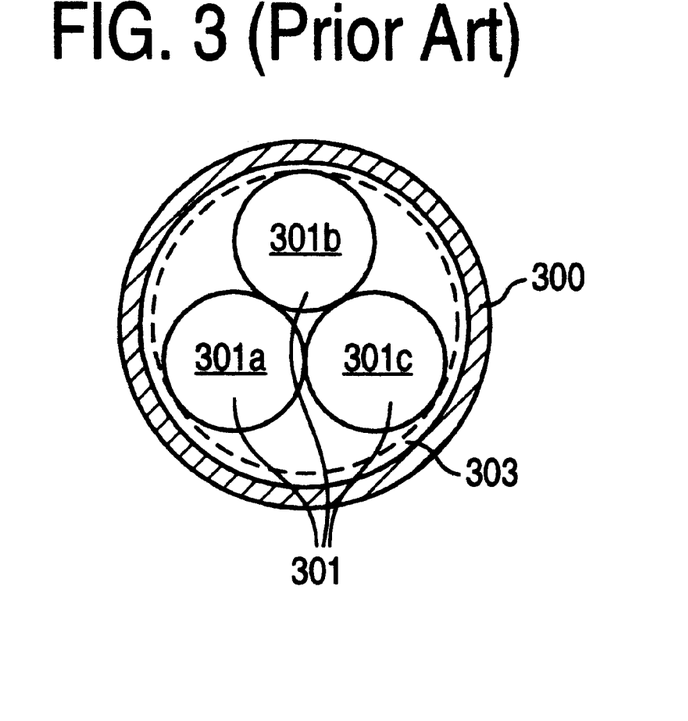
FIG. 3 illustrates another prior art guidewire that is made of three braided wires.

FIG. 3 illustrates a cross-section of another prior art embodiment in which the guidewire 301 is made of three separate wires 301a–c, which are braided together. Each wire may have a diameter of approximately 0.008 inches while the internal diameter of the catheter 300 may be 0.032 inch. FIG. 3 illustrates one disadvantage of the prior art systems. The length of the guidewire cannot be changed without altering or compromising the structural integrity of the guidewire. For example, guidewire 301 of FIG. 3 cannot be cut without compromising or destroying the structural integrity of the guidewire 301 as its three wires 301a–c will unravel and separate. The same is true for the guidewire 200 of FIG. 2 and its three components, 205, 207 and 209.

As is evident from FIGS. 1, 2 and 3, the fluid flow area (104, 203, 303) around each respective guidewire (102, 200, 301) is severely restricted as the diameter of the guidewire approaches the internal diameter of the catheter. Many prior art guidewires are made of metal so that the guidewire may not be cut when adjustability of the catheter length is desired. As a result, in these prior art embodiments, the guidewire is adjusted by first withdrawing the guidewire from the proximal end of the catheter and then cutting the catheter. These catheters thus require extra-tedious manipulations before being able to use them.

Smaller fluid flow due to decreased area between the guidewire (or stylet) and the inner wall of the catheter is undesirable. Adequate fluid flow is necessary for the flushing solution to aid insertion and removal of the guidewire (or stylet) in the catheter. In addition, unhindered fluid flow helps prevent friction between the guidewire (or stylet) and the inner wall of the catheter. Thus, it is desirable that a guidewire (or stylet) serves as a stiffening member in a medical device, such as for example, a PICC catheter, during insertion of the medical device. It is also desirable that the shape of the stiffening member helps increase fluid flow around the guidewire (or stylet) disposed within the medical device.

SUMMARY

The present invention describes a stiffening member that allows an increase in the fluid flow area within a medical device, such as a catheter. In one embodiment, the stiffening member is an elongated, substantially rectangular stylet that is disposed within the catheter, such that the stylet can occupy less than half of the lumen area of the catheter. As a result, adequate fluid flow is allowed between the stylet and the inner wall of the catheter. This increases patient comfort. In a preferred embodiment, the stylet is made of substantially flat stock such that in cross-section, the longer dimension of the stylet closely approximates or is slightly smaller than the internal diameter of the catheter. Furthermore, in the preferred embodiment, the flat stock is twisted over the length of the stylet to achieve equal rigidity or bendability over the entire length of the stylet in any axis. Different pitches (i.e., number of twists or turns per inch) may be used to obtain stylets with different degrees of rigidity. Moreover, the pitch within a single stylet may be varied to create multiple stiffnesses within a single stylet. For example, the proximal end can have a greater pitch than the digital end of a stylet to create a softer proximal end. This is beneficial since the proximal end is inserted first into the patient.

The elongated, substantially rectangular stylet comprises the majority of the cross-sectional area of the substantially rectangular stiffening member. Substantially rectangular, as defined, can also include a cross-sectional area of a single element that is shaped like various versions of an I-beam, a dog-bone, an ellipse, an oval, and a rectangle. The cross-section of the substantially rectangular stylet has a long first axis and a short second axis that is not aligned with the first axis. The first and second axes, however, are coupled together and are part of a single element stylet.

The cross-sectional area of the stiffening member is usually such that one dimension (the "long" dimension) is at least twice or most preferentially, eight times the length of the other dimension (the "short" dimension); in this way, the stiffening member is substantially rectangular at least in cross-sectional view. This allows the flushing fluid to flow through at least half of the lumen area within the catheter, and more preferably through about 80% of the catheter's lumen area.

In another embodiment, a cross-sectional area of the elongated stylet is a percentage up to 65% of a cross-sectional area of the catheter's lumen. The available fluid flow area is the area not occupied by the elongated stylet within the catheter's lumen. The cross-sectional area of the elongated stylet is formed substantially by a single stiffening member. In yet another aspect of the present invention, a coating can be placed around the single stiffening member. The coating does not substantially decrease the fluid flow around the stylet. Moreover, the coating can be selected from a group consisting of a hydrogel, or Teflon™, which applies to a tetrafluorethylene fluorocarbon polymer and a fluorinated ethylene-propylene resin.

BRIEF DESCRIPTION OF THE DRAWINGS

The present invention is illustrated by way of example and not by way of limitation in the figures of the accompanying drawings in which like references indicate similar elements. In addition, for the sake of clarity, certain elements in a figure may appear larger and are not drawn to scale.

DETAILED DESCRIPTION

An apparatus for enhancing fluid flow within a medical device, such as a catheter is described. In the following description, numerous specific details are set forth in order to provide a thorough understanding of the present invention. It will be apparent, however, to one skilled in the art that the present invention may be practiced without these specific details. In other instances, well-known structures may not be shown in order to avoid unnecessarily obscuring the present invention. In other cases, specific examples are described and shown in order to thoroughly describe the invention. It will be appreciated that these specific examples are for the purpose of explanation and that alternative embodiments will be understood by those in the art.

The present invention provides several advantages over the prior art. The present invention increases fluid flow within a catheter without sacrificing the mechanical stiffening provided by the stylet. This is especially important in flushable guidewire systems where unhindered flow of a flushing solution is essential. The flushing solution helps reduce the friction between the guidewire (or stylet) and the inner wall of the catheter while the catheter is twisting and turning through the blood vessel. In addition, the flushing solution aids in manipulating and finally removing the stylet. This reduces the possibility that the guidewire may become jammed in the catheter and require removal of the catheter from the patient. It is also helpful to infuse fluid through the catheter while advancing the catheter through the patient. This is because the fluid dilates the blood vessel and makes it easier for the catheter to advance, particularly if there is an obstruction in the vessel. Thus, by increasing the area available for fluid flow between the stylet and the inner wall of the catheter, many of these problems are prevented. Furthermore, increased fluid flow within the catheter also increases patient comfort. Moreover, for catheters with small internal diameters, the present invention allows maximum stylet effectiveness while still retaining full flushing capabilities.

The present stylet invention may also be easily cut to adjust the length of the catheter without compromising or destroying the structural integrity of the stylet. For example, the structural integrity of the prior art guidewires 200 and 301 of FIGS. 2 and 3 are lost if the guidewires 200 and 301 are cut, because components (205, 207, 209 and 301a–c, respectively) will unravel and separate. This should also result in significant time savings, because unlike the prior art, the stylet of the present invention does not need to be removed before the catheter is cut. Moreover, the stylet does not need to be presized to fit the exact length of the catheter. Because a physician or a nurse cannot usually determine with absolute accuracy the length of catheter needed for a particular patient, the present invention provides additional flexibility and time-efficiency to the busy medical practitioner. Finally, the present stylet is much easier to manufacture than prior art examples since it is a single element. For example, the prior art guidewires illustrated in FIG. 3 and in FIG. 2A comprise three elements. Thus, the present invention should decrease manufacturing costs and also decrease overall health-care costs.

Figure 4:
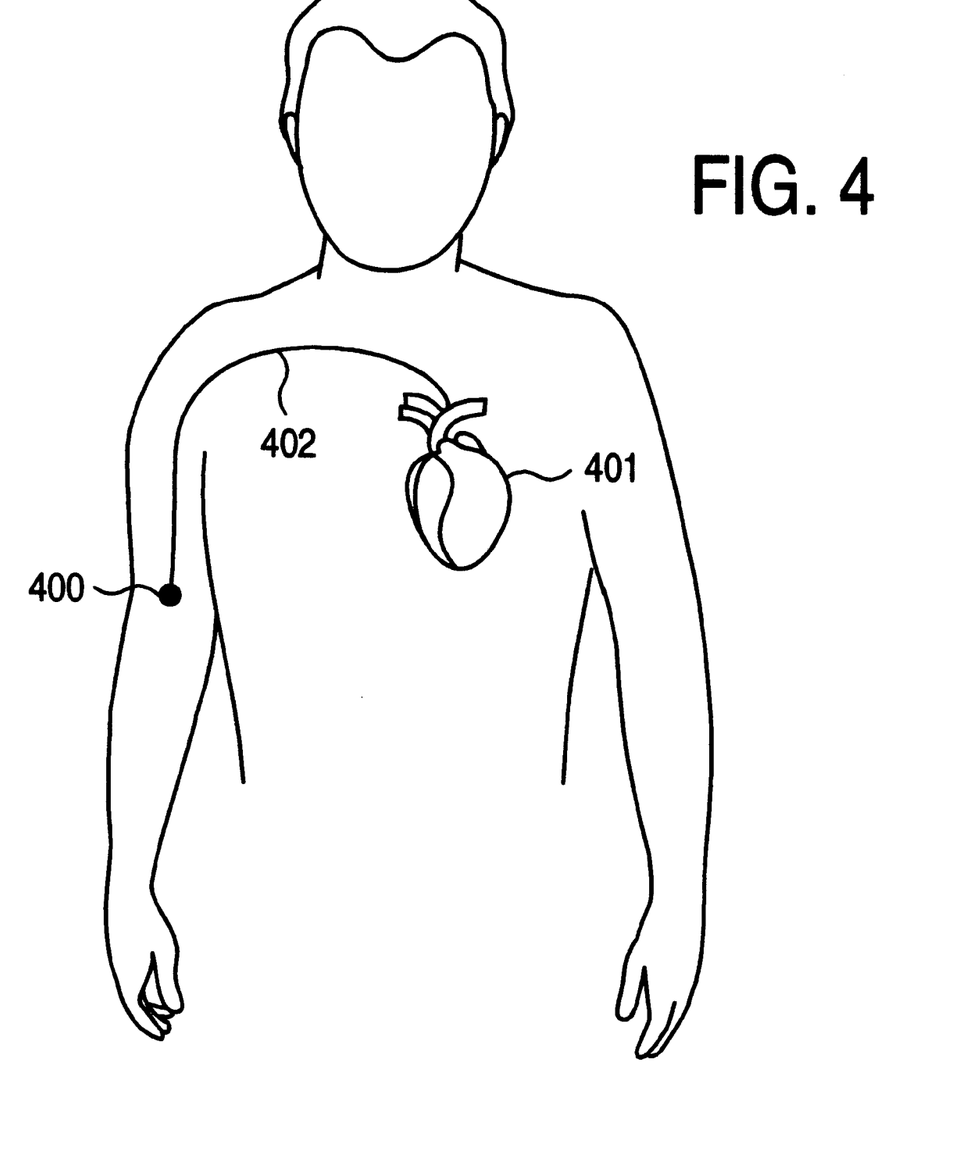
FIG. 4 illustrates placement of a PICC catheter.

One embodiment of the present invention is particularly useful in peripherally inserted central catheters (PICCs), one of which is illustrated in FIG. 4. A PICC 402 is used when long-term-vascular access is required, for example, more than two weeks, in order to avoid traumatizing the patient with multiple injections. As shown in FIG. 4, a PICC is a longer catheter that is often inserted midway on a patient's arm 400 initially and the end of the catheter is often placed in the superior vena cava of the heart 401. A PICC must often travel anywhere from six to twenty inches, depending on the size of the patient, before its distal end (the end farthest from the original entry point) reaches its final indwelling point. As a result, a stylet is often used to help stiffen the catheter, which is often made of a soft biocompatible material. The soft construction of a catheter often causes the PICC to collapse and/or bend before entering a patient's veins. Thus, a flexible metal stylet enables one to more quickly and efficiently insert a PICC. Since the PICC 402 and thus the stylet, must travel through many natural barriers and a fairly long distance through the patient's body, maximum fluid flow between the stylet and the catheter is necessary for increased patient comfort and decreased incidents of trauma to the patient's veins.

Figure 5A:
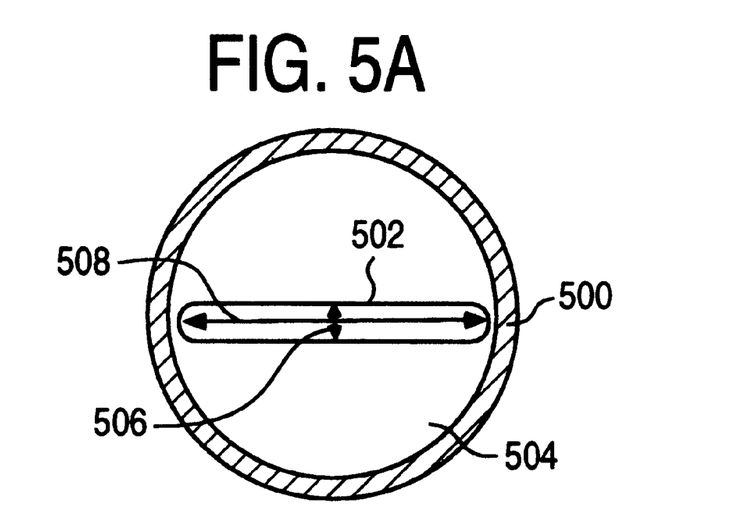
FIG. 5A illustrates a cross-section of one embodiment of the present invention.

Referring to FIG. 5A, a cross-section of one embodiment of the present invention is illustrated. A single-elongated, substantially rectangular stiffening member 502 is shown within a catheter 500. Substantially rectangular is defined to mean that in cross-section, a first dimension or first axis 508 of the stiffening member 502 is at least twice the length of a second dimension or second axis 506 that is perpendicular to the first dimension.

In particular, first axis 508 is eight-times the length of second axis 506. For example, if the internal diameter of catheter 500 is 0.035th of an inch and the first axis 508 is about 0.032th of an inch and the second axis 506 is 0.004th of an inch, then stiffening member (in cross-section) occupies about 16.8% of the cross-sectional area of the lumen of catheter 500. Thus, a cross-section of the stiffening member 502 results in a substantially rectangular shape. It is to be appreciated that other dimensions for first axis 508 and second axis 506 can be used within the scope of the present invention. For example, first (or long) axis 508 could be six times longer than second (or short) axis 506. In addition, first axis 508 provides most of the bending stiffness of elongated stiffening member 502. Bending stiffness is the force required to bend an object. For example, steel has a greater bending stiffness than rubber. A fluid flow area 504 through at least more than half of the internal area or lumen of the catheter 500 is shown. The fluid flow area 504 is much greater than the prior art fluid flow areas (104, 203 and 303) illustrated in FIGS. 1, 2A and 3, respectively.

Although stiffening member 502 can operate as a stylet by providing column strength to the catheter 500 to aid insertion of the catheter, its substantially rectangular shape (as seen in cross-section) does not greatly reduce the fluid flow like prior art guidewires. In an exemplary embodiment, the stylet has a cross-sectional area that is defined substantially by the cross-sectional area of the elongated, substantially rectangular stiffening member 502. It will be appreciated that an additional treatment, such as a coating (e.g., a hydrogel or a Teflon™ or Teflon™-type material) can be placed around the stiffening member 502. The term TeflonTm applies to tetrafluorethylene fluorocarbon polymers and fluorinated ethylene-propylene resins. The coating should not substantially increase the diameter or cross-sectional area of the stiffening member 502. Thus, the coating should not dramatically decrease fluid flow area 504.

In FIG. 5A, a cross-section of the flat section of stiffening member 502 is shown that is less than the internal diameter of the catheter 500. It is to be appreciated that the flat section of stiffening member 502, as shown in cross-section, may also closely approximate the internal diameter of catheter 500 in another embodiment. Stiffening member 502 may be made of metal or plastic. It will be apparent to one skilled in the art that stiffening member 502 may be made of any bio-compatible material that provides column strength to catheter 500 with minimal irritation to the patient's blood vessel. It will also be apparent to one of skill in the art that the present invention may also be used in other catheters, such as, a mid-line catheter and is not restricted to PICCs.

Figure 5B:
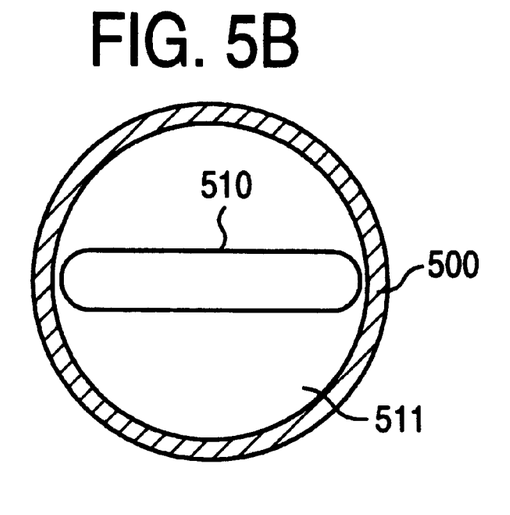
FIG. 5B illustrates a cross-section of a larger embodiment of FIG. 5A.

A cross-section of another embodiment of a stiffening member is shown in FIG. 5B. Stiffening member 510 is disposed within the lumen of catheter 500 with a fluid flow area 511. In this particular embodiment, the length of the long axis or first axis of stiffening member 510 is about four times greater than the length of its short axis or second axis. For example, if stiffening member 510 had a first axis of 0.032th of an inch, a second axis of about 0.008th of an inch and the internal diameter of the catheter is 0.035th of an inch, then the cross-sectional area of stiffening member 510 is about 27% of the cross-sectional area of the lumen for catheter 500. This means that there is a fluid flow area 511 of about 73% in an embodiment with those dimensions.

Figure 5C:
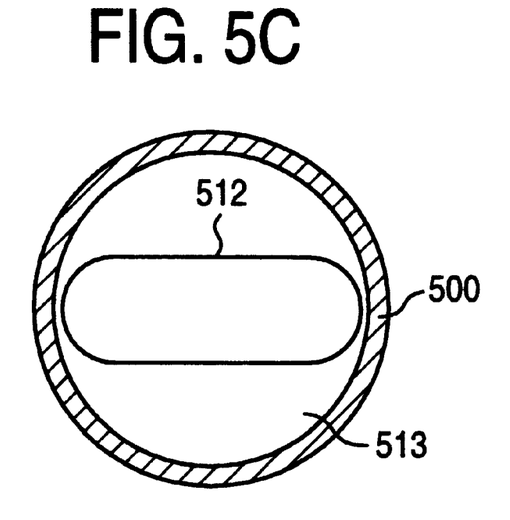
FIG. 5C illustrates a cross-section of an even larger embodiment of FIG. 5A.

The cross-section of an even larger embodiment of a similarly shaped stiffening member is illustrated in FIG. 5C. The stiffening member 512 is disposed within the lumen of catheter 500. The fluid flow area 513 of FIG. 5C is less than the fluid flow area 511 of FIG. 5B because the size of the stiffening member has increased. For example, if the internal diameter of catheter 500 is 0.035th of an inch, the long axis or first axis of stiffening member 512 is 0.032th of an inch and the short axis or second axis of stiffening member 512 is 0.016th of an inch, then stiffening member 512 occupies about 48% of the lumen area of the catheter 500 in cross-section. Thus, FIG. 5C illustrates an embodiment where the long axis is about twice the length of the short axis. This results in a fluid flow of about 52% of the cross-sectional area of the lumen of the catheter 500. The ratio of long axis to short axis in the crosssection of the various stiffening members shown in FIGS. 5A–C is meant to be illustrative and not limiting.

Figure 6A:
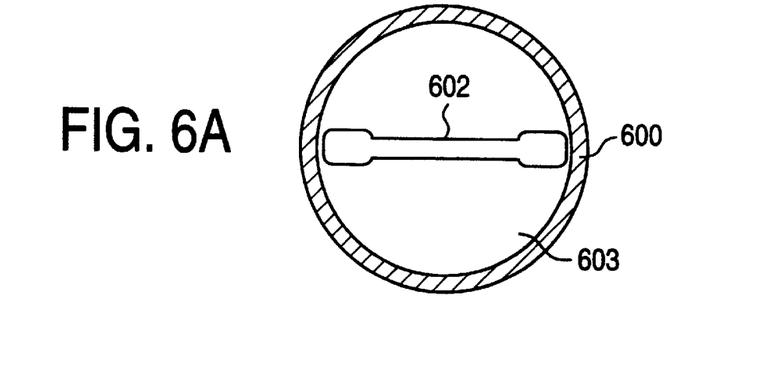
FIG. 6A illustrates a cross-section of a dog-bone or dumbbell-shaped embodiment of the present invention.
Figure 6B:
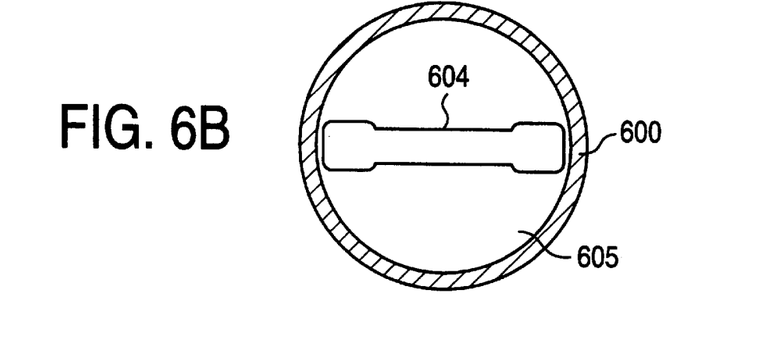
FIG. 6B illustrates a cross-section of another dog-bone or dumbbellshaped embodiment of the present invention.
Figure 6C:
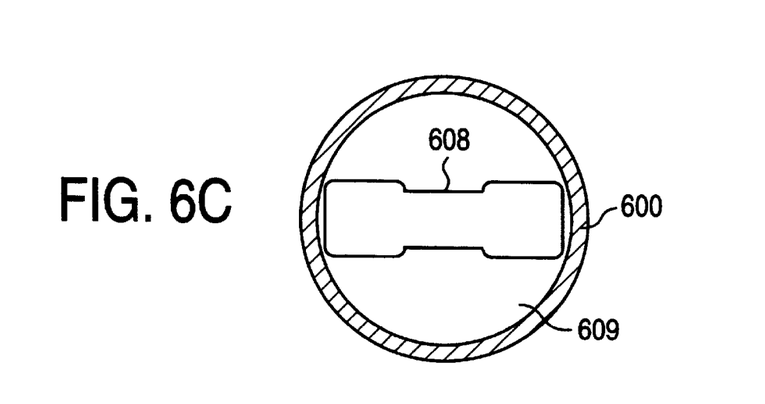
FIG. 6C illustrates a cross-section of yet another dog-bone or dumbbell-shaped embodiment of the present invention.

FIGS. 6A–C illustrate a cross-section of a series of different dog-bone or dumbbell-shaped embodiments for a stiffening member. In all three figures, FIGS. 6A–C, it will be assumed that the internal diameter of the catheter 600 is 0.035th of an inch for an exemplary catheter. In addition, it will also be assumed, for illustrative purposes, that the long axis (defined like 508 of FIG. 5A) of the stiffening member 602, 604, and 608 of each respective figure (FIGS. 6A–C), is 0.032th of an inch.

In FIG. 6A, for example, the thin middle portion of stiffening member 602 can have a thickness of about 0.004th of an inch and the two thicker end portions of stiffening member 602 (which are contiguous to the middle portion) can be about 0.008th of an inch in an exemplary embodiment. If one considers the thickness of the end portions to be a "short axis", in this case 0.008th of an inch, then the "long axis" of 0.032th of an inch is four times greater than the short axis. In this exemplary embodiment, the stiffening member 602, in cross-section, occupies about 16.8% of the cross-sectional area of the lumen of catheter 600. Thus, the fluid flow area 603, in this embodiment, is about 83.2%, which is a significant increase over the prior art.

Referring to FIG. 6B, the middle portion of stiffening member 604 is wider than the middle portion of FIG. 6A, such that the cross-sectional area of stiffening member 604 is increased to about 27% of the cross-sectional area of the lumen of catheter 600. The short axis (defined by the thickness of the two end portions), however, is slightly smaller than the short axis of FIG. 6A. Consequently, the fluid flow area 605 has decreased accordingly to about 73% of the cross-sectional area of the lumen of catheter 600.

In yet another embodiment, as illustrated in FIG. 6C, the middle portion and the two end portions of stiffening member 608 are further increased in size. For example, the middle portion can be about 0.012th of an inch and the two end portions ("short axis") can be about 0.012th of an inch, which means the long axis of 0.032th of an inch is about 2.67 times greater than the short axis in this embodiment. According to these exemplary dimensions, the stiffening member 608 occupies in cross-section, about 38.6% of the cross-sectional area of the lumen of catheter 600. Thus, the fluid flow area 609 is about 61.4% of the cross-sectional area of the lumen of catheter 600. Thus, FIGS. 6A–C illustrate how changing the size of the substantially rectangular dumbbell-shaped or dog-bone embodiment of the stiffening member affects the resulting fluid flow area. It is to be noted that the fluid flow area is still greater than the fluid flow area available in prior art FIG. 1, which had a fluid flow area of about 30%.

Figure 7A:
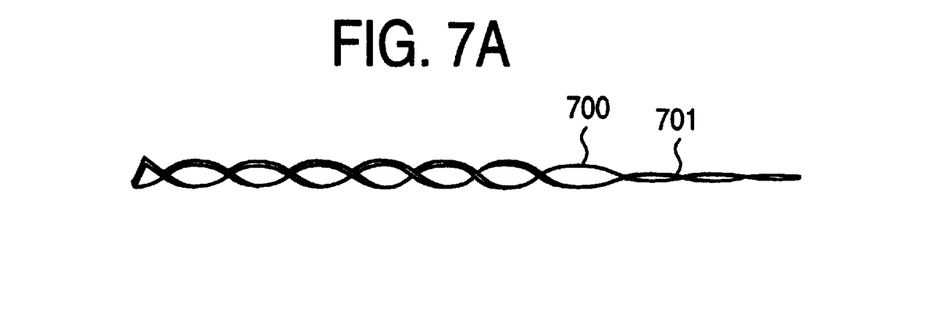
FIG. 7A illustrates another view of the stiffening member 502 of FIG. 5A.

Another view of the present invention is illustrated in FIG. 7A. In a preferred embodiment, the stiffening member 700 or stylet is made of substantially flat rectangular stock that can be twisted to provide equal rigidity or bendability in all directions. Substantially flat, in this case, is defined to mean without any major curves that will change the substantially rectangular cross-section of the stiffening member 700. It will be apparent to one skilled in the art that the pitch (i.e., twists or turns per inch) may be varied to change the stiffness of the stylet. In addition, the tip 701 shown in FIG. 7A is narrowed but still maintained the same pitch as the rest of the stiffening member 700. It is to be appreciated that the tip 701 of stiffening member or stylet 700 can have different shapes, for example, a flat-shaped tip or a rounded tip. It will also be apparent to one of skill in the art that both ends of the stylet could have, for example, a flat-shaped tip or a rotary-swaged rounded tip. The embodiment shown in FIG. 7A is meant to be illustrative and not limiting.

Figure 7B:
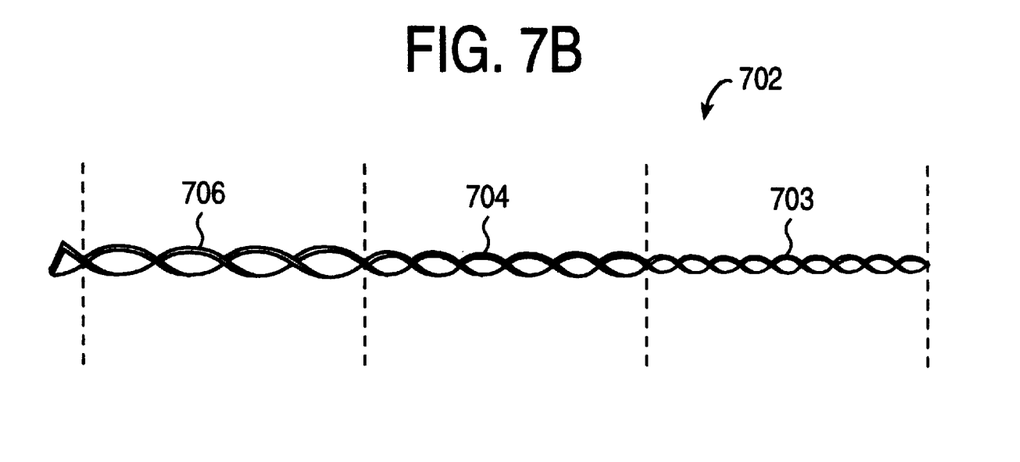
FIG. 7B illustrates a side view of another embodiment of the present invention.

A side-view of another embodiment of the present invention is shown in FIG. 7B. A stiffening member 702 having three different pitches is illustrated. The proximal portion 703 of stiffening member 702 has the greatest pitch and is thus, the softest portion of stiffening member 702. The distal portion 706 has the smallest pitch and consequently, is the stiffest portion of stiffening member 702. Mid-section 704 has a pitch that is between the pitch of proximal portion 703 and of distal portion 706. Thus, mid-section 704 is stiffer than proximal portion 703, but softer than distal portion 706. It is to be appreciated that any number of different pitches can be obtained within a single stiffening member 702.

Figure 8:
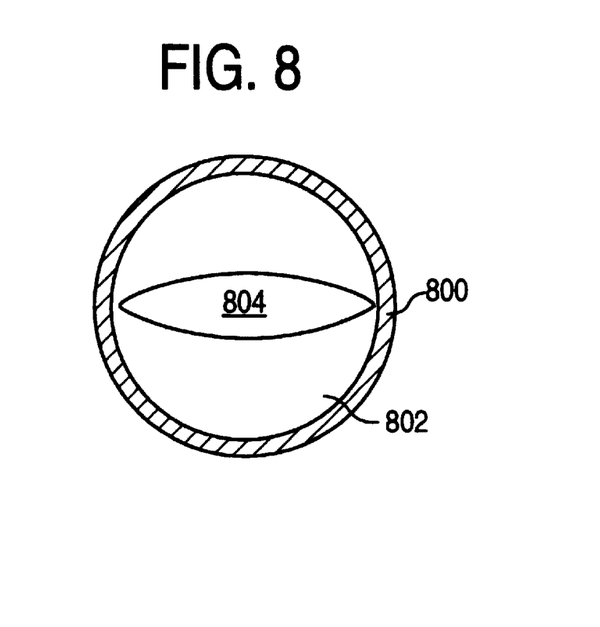
FIG. 8 illustrates a cross-section of yet another embodiment of the present invention.

Referring to FIG. 8, a cross-section of another embodiment of the present invention is illustrated. A single elongated, substantially rectangular stiffening member 804 is shown within a catheter 800. In this embodiment, the substantially rectangular shaped member is an elliptical-shaped member 804 that can be twisted, in one embodiment, to provide equal rigidity along any axis. The elliptical shape fits within "substantially rectangular" as defined earlier. A cross-section of elliptical stiffening member 804 has a first axis that is longer than a second-axis that is perpendicular to the first-axis. In other words, in cross-section, the first-axis is the "long" dimension and the second-axis is the "short-"dimension of substantially rectangular stiffening member 804. The portion of stiffening member 804 that is aligned along the first axis provides most of the mechanical strength. The diameter of the cross-section of the first-axis can closely approximate or be less than the diameter of the catheter. Moreover, elliptical stiffening member 804 can be formed so that more than half of the lumen area of catheter 800 is available for fluid flow 802.

A cross-section of stiffening member 804 can also substantially define the cross-sectional area of the stylet. It will be appreciated that an additional treatment, such as a coating (e.g., a hydrogel or Teflon™) can be placed around the stiffening member 804. The coating does not substantially increase the diameter or cross-sectional area of the stiffening member 804. In other words, the coating should not dramatically decrease fluid flow area 802.

The pitch of elliptically-shaped stiffening member 804 may be varied to change the stiffness of the stylet. For example, stiffening member 804 can be twisted at one pitch on its proximal end and another pitch at its distal end to produce different stiffnesses within a single stiffening member 804. Furthermore, one end or both ends of elliptically-shaped member 804 may have many different shapes. For instance, one end or both ends can be narrowed to form a tip. The tip can have different configurations, for example, a flat-shaped tip or a rounded tip that can be obtained by a rotary swage. Thus, FIG. 8 is meant to be illustrative and not limiting.

Figure 9A:
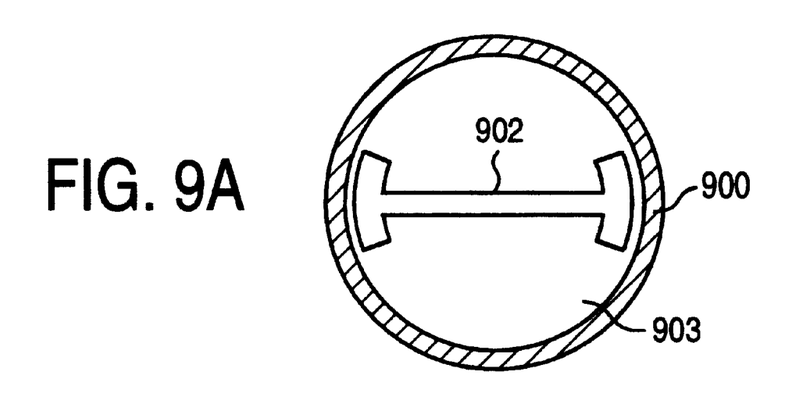
FIG. 9A illustrates a cross-section of an I-beam embodiment of the present invention.
Figure 9B:
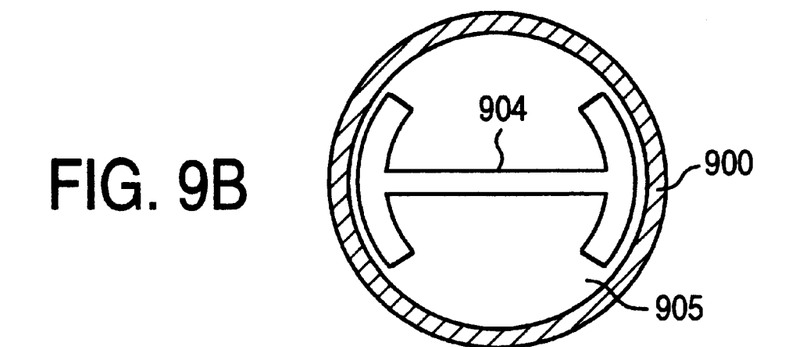
FIG. 9B illustrates a cross-section of another I-beam embodiment of the present invention.
Figure 9C:
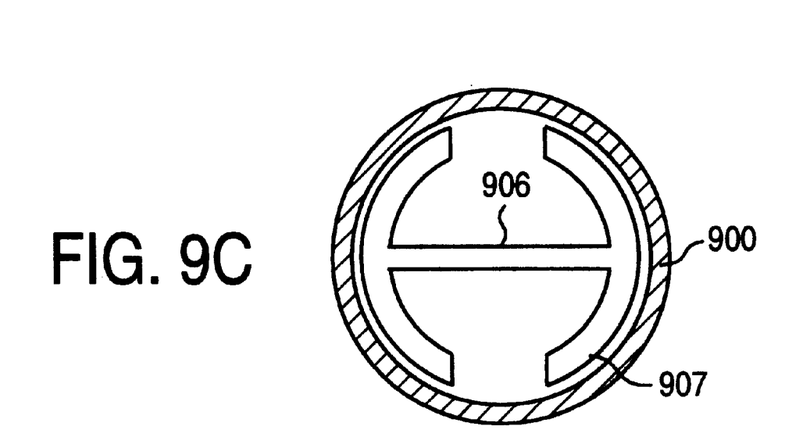
FIG. 9C illustrates a cross-section of yet another I-beam embodiment of the present invention.

FIGS. 9A–C illustrate how the present invention can be defined by how a cross-sectional area of a stylet is a certain percentage of the cross-sectional area of the catheter's lumen. More specifically, FIGS. 9A–C illustrate a cross-section of an I-beam embodiment of the present invention relative to the cross-section of the catheter's lumen in which the I-beam embodiment is disposed. For example, the internal diameter of the catheter 900 can be 0.035th of an inch, and the axis along the length of the two ends can increase from about 0.012th of an inch in FIG. 9A, to about 0.024th of an inch in FIG. 9B, and then to about 0.030th of an inch in FIG. 9C. It is to be appreciated that other variations of an I-beam are also covered by the present invention. FIGS. 9A–C illustrate how the fluid flow area decreases as the cross-sectional area of the stiffening member increases from FIGS. 9A–C. In FIG. 9A, stiffening member 902 has a cross-sectional area that is about 18% of the cross-sectional area of the lumen of catheter 900. As a result, there is a fluid flow area 903 that is about 82% of the cross-sectional area of the lumen of catheter 900.

As a contrast, in FIG. 9B, the stiffening member 904 is larger and its cross-section occupies about 27.2% of the cross-sectional area of the lumen of catheter 900. Thus, the fluid flow area 905 is about 72.8% of the cross-sectional area of the lumen of catheter 900. In FIG. 9C, the ends of the I-beam have increased such that the cross-sectional area of the stiffening member 906 has increased to about 38.6% of the cross-sectional area of the lumen of catheter 900. As a result, the fluid flow area 907 is about 62.4% of the cross-sectional area of the lumen of catheter 900, which is still better than the fluid flow area of the single-element guidewire in the prior art shown in FIG. 1. It will be apparent to one skilled in the art that the percentages given for FIGS. 9A–C are illustrative and not meant to be limiting.

It is to be appreciated that an additional treatment, such as a coating (e.g., a hydrogel or a Teflon™ or a Teflon™-type material) can also be placed around each of the stiffening members (902, 904, 906) illustrated in FIGS. 9A–C, respectively. This coating should not substantially increase the cross-sectional area of the stiffening member or decrease dramatically the fluid flow area. It will be further appreciated that each of the stiffening members (902, 904, 906) shown in FIGS. 9A–C can be twisted and can have varying pitches within a single stiffening member. Furthermore, although not shown, a stiffening member that is shaped like a circular or ellipsoidal O-ring would also fall within the scope of the present invention.

Figure 10:
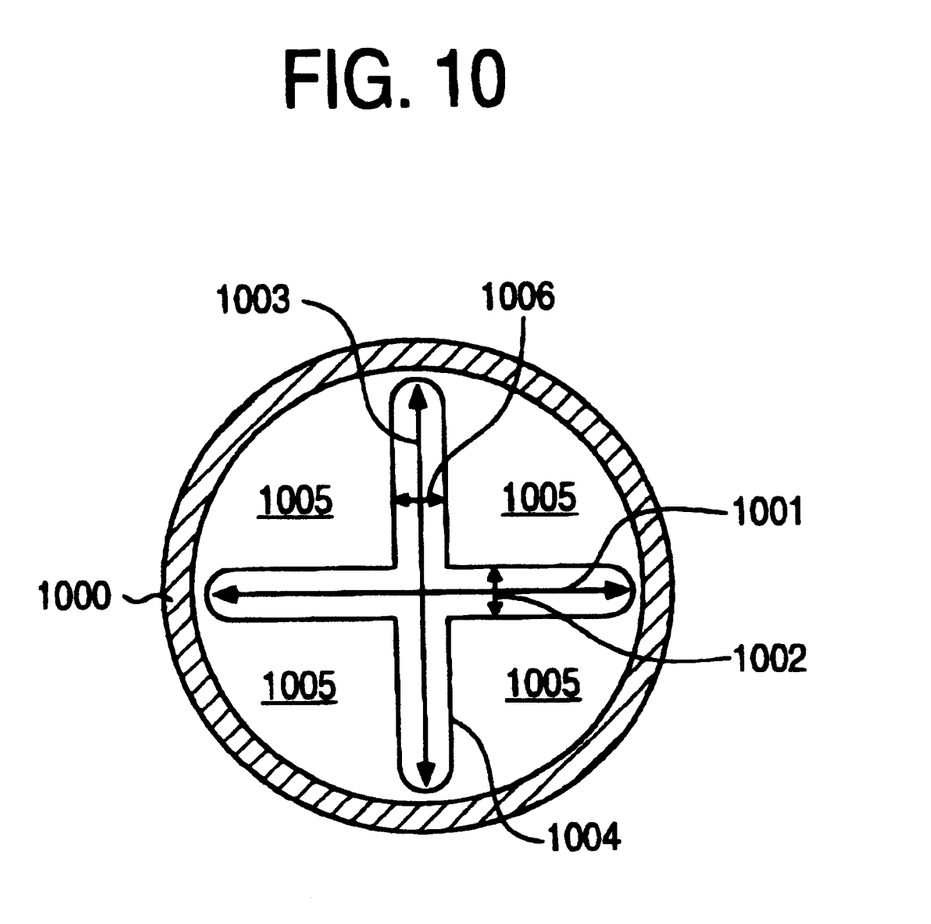
FIG. 10 illustrates a cross-section of another embodiment of the present invention.

A cross-section of an "X-shaped" or "cross-shaped" embodiment of the present invention is illustrated in FIG. 10. An "X-shaped" stiffening member 1004 formed of two substantially rectangular elongated members is disposed within catheter 100 with fluid flow area 1005. One substantially rectangular elongated member has a long axis 1003 that is at least twice the length of its short axis 1006. In addition, the second substantially rectangular elongated member also has a long axis 1001 that is at least twice the length of its short axis 1002. It is to be appreciated that long axis 1001 and long axis 1003 and each of their respective short axes (1002, 1006) do not have to be equivalent as shown in FIG. 10. For example, long axis 1001 could be shorter than long axis 1003 and short axis 1002 could be wider than short axis 1006. It is to be noted that stiffening member 1004 can be twisted at one pitch or several different pitches throughout its entire length. Furthermore, it is also to be appreciated that an additional treatment, such as a coating (e.g., a hydrogel or a Teflon™ or Teflon™-type material) can be placed around stiffening member 1004. The coating should not substantially increase the diameter or cross-sectional area of stiffening member 1004. Thus, the coating should not greatly decrease the fluid flow area 1005.

The foregoing description provides an example of a stiffening member, such as a stylet, disposed within a medical device, such as a PICC. It will be apparent to one of skill in the art that the medical device can be, for example, a stent, a cannula, a scope or any other device that uses a stylet or a guidewire. It will be appreciated that numerous modifications may be made in practicing the present invention without departing from the spirit and scope of the invention, which is defined by the following claims.

What is claimed is:

1. A vascular access device, comprising:

a catheter having a lumen; and an elongated stylet disposed within the lumen, wherein the stylet has a substantially rectangular cross-section and an elongated portion extending through the lumen that, in cross-section, closely approximates an internal diameter of the lumen and allows fluid to flow through more than half of the lumen around the stylet.

2. The vascular access device of claim 1, wherein a cross-section of the elongated stylet has a substantially flat rectangular shape.

3. The vascular access device of claim 1, wherein the elongated stylet has a narrowed tip.

4. The vascular access device of claim 1, wherein the elongated stylet includes a coating around a stiffening member, wherein the stiffening member comprises most of the cross-section of the elongated stylet, and wherein the coating does not substantially decrease the fluid flow around the stylet.

5. The vascular access device of claim 4, wherein the coating is selected from a group consisting of a hydrogel, a tetrafluoroethylene fluorocarbon polymer and a fluorinated ethylene-propylene resin.

6. The vascular access device, comprising:

a catheter having a lumen; and an elongated stylet disposed within the lumen, wherein a cross-sectional area of an elongated portion of the elongated stylet extending through the lumen closely approximates an internal diameter of the lumen, the cross-sectional area is a percentage up to 65% of a crosssectional area of the lumen, and the cross-sectional area of the elongated stylet is formed substantially by a single substantially rectangular stiffening member.

7. The vascular access device of claim 6, wherein the cross-sectional area of the elongated stylet's percentage is in the range of about 16% to about 50% of the cross-sectional area of the lumen.

8. The vascular access device of claim 6, wherein a cross-section of a fluid flow area between the cross-section of the elongated stylet and the cross-section of the lumen results in a cross-sectional fluid flow area of at least 35% of the cross-sectional lumen.

9. The vascular access device of claim 6, wherein the elongated stylet can be cut to a predetermined length.

\* \* \* \* \*